United States Patent [19]
Clinton

[11] 4,022,196
[45] May 10, 1977

[54] PENILE PROSTHETIC APPARATUS

[76] Inventor: Robert E. Clinton, 6403 S. 5th Ave., Phoenix, Ariz. 85041

[22] Filed: June 1, 1976

[21] Appl. No.: 691,391

[52] U.S. Cl. .............................................. 128/79
[51] Int. Cl.² ......................................... A61F 5/00
[58] Field of Search ..................... 128/79, 68, 68.1

[56] References Cited
UNITED STATES PATENTS

| | | | |
|---|---|---|---|
| 837,993 | 12/1906 | Williams | 128/79 |
| 1,270,880 | 7/1918 | Scheinkman | 128/79 |
| 1,362,398 | 12/1920 | Crawford et al. | 128/79 |
| 1,511,572 | 10/1924 | Marshall | 128/79 |
| 2,868,192 | 1/1959 | Dannen | 128/79 |

Primary Examiner—Lawrence W. Trapp
Attorney, Agent, or Firm—H. Gordon Shields

[57] ABSTRACT

Penile prosthetic apparatus which includes a relatively rigid base to support the apparatus against the male body and into which fits a male penis for enhancing male and female sexual relations.

7 Claims, 6 Drawing Figures

U.S. Patent    May 10, 1977    4,022,196
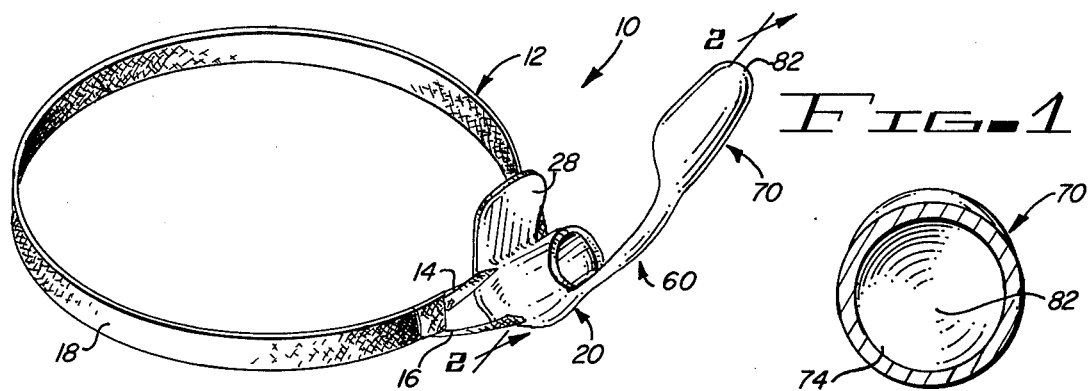
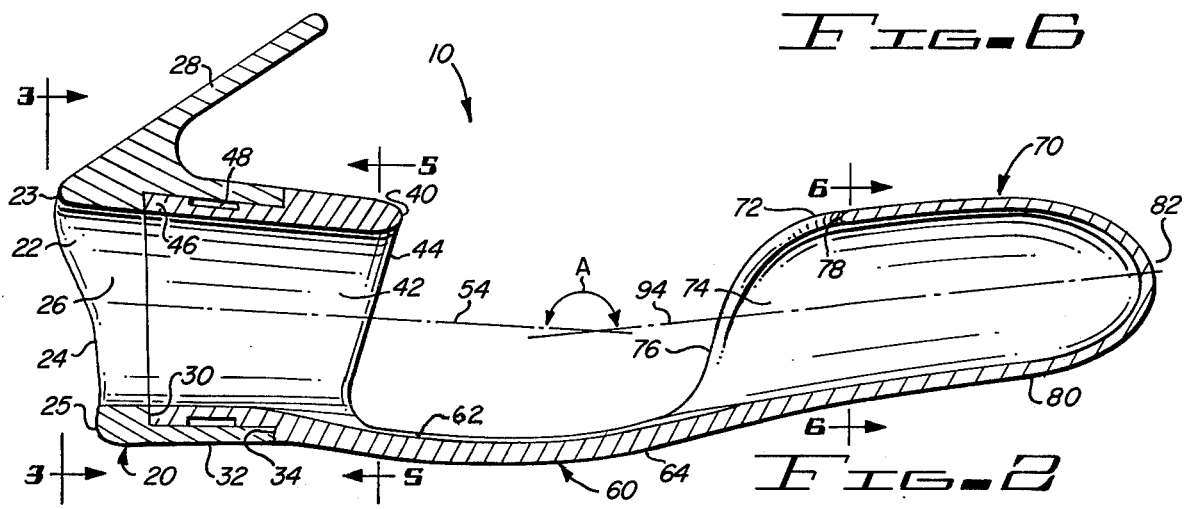
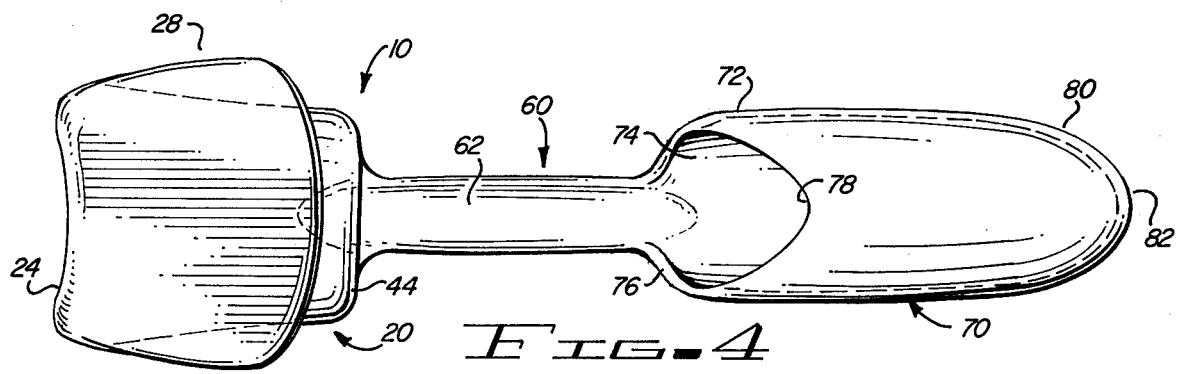
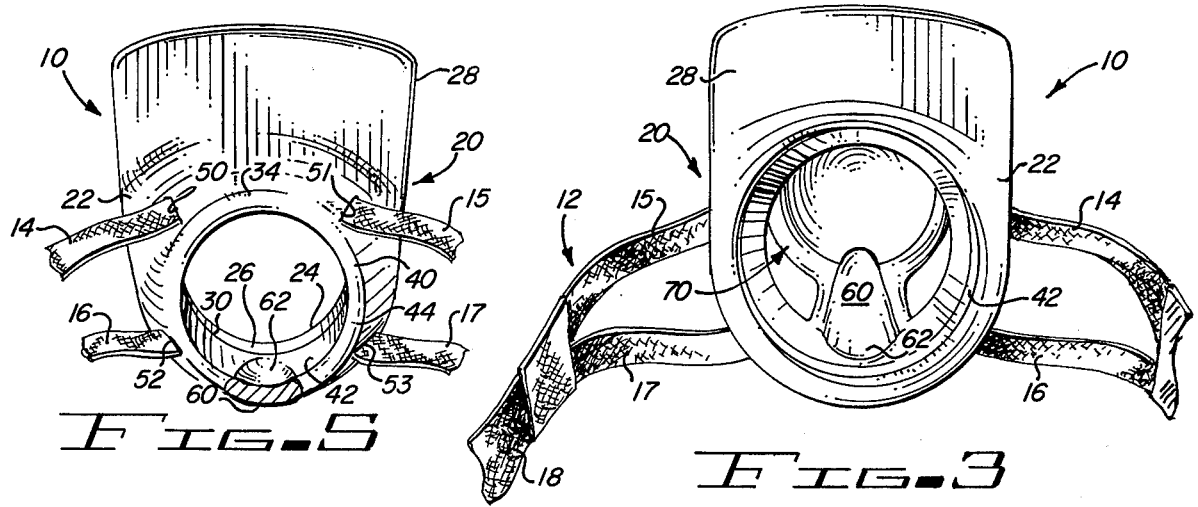

PENILE PROSTHETIC APPARATUS

BACKGROUND OF THE INVENTION

1. Field of the Invention

This invention relates to a prosthetic penis and, more particularly to an elongated, artificial penis supported against the male user's body and enclosing a portion of his penis for facilitating sexual relations with a female partner.

2. Description of the Prior Art

The prior art recognizes the need for an artificial penis, or a prosthetic penile apparatus for the purpose of elongating a penis artificially to facilitate mutually satisfactory sexual relations between a male and a female partner. The term "mutually satisfactory" includes the concept of physical, emotional, and psychological needs. A male penis may be inadequate for any number of reasons, such as infantilism, impotence, accidental disfigurement, or, and typically most common, simply hereditary factors.

According to textbook anatomy and the results of various types of studies, the "average" male penis or organ varies in length between about 5½ and 6 inches, and in diameter of about one inch to slightly larger, when erected, as under sexual stimulation. Moreover, due to physical or psychological factors, a male may not always be able to achieve a full erection. Accordingly, in order to accommodate his female partner, and enhance sexual relations, a penile prosthetic device may be needed.

U.S. Pat. No. 1,511,572 illustrates one embodiment of such apparatus. The apparatus includes a generally rigid splint which includes a relatively soft and yielding inner portion which contacts the male organ. A support member serves as a support for the splint and is detachably secured to the splint. The support member is in turn connected to a belt which encircles the body of a wearer. With the belt in place, the support member is disposed in such a form as to embrace a male gential organ near the base of the organ and to conform to the adjacent pelvic and abdominal contour.

U.S. Pat. No. 3,397,689 describes an introducer sheath adapted to receive a male organ. The sheath is rotatably affixed to a base plate which in turn may be secured to the wearer's body with a strap. The sheath includes an opening to the lateral wall which serves to provide direct contact between the male wearer and his female partner.

U.S. Pat. No. 3,759,254 discloses a different type of member which is designed to encompass the male penis and the scrotum. The portion which encloses the penis is a relatively resilient an flexible tubular portion with a stiffening rib extending along the longitudinal axis of the tubular portion and at the top of the apparatus. The stiffening rib comprises a prosthetic aid during copulation.

A problem in the prior art is in providing suitable support for the male wearer or user of the apparatus. Two factors must be kept in mind, one the factor of comfort to both of the partners, and the second factor the support means with respect to the natural anatomical male structure. The apparatus should be supported against the male body at an angle substantially the same as the angle at which a mature, fully erected penis extends. However, such apparatus must in turn be supported by the male body so as not to interfere with the comfort of either partner in terms of undesirable pressure or angles.

The apparatus of the present invention provides a prosthetic apparatus capable of two orientations on a male including a "downward" position to facilitate entry of the penis into the apparatus, and a second or "upward" position in which the penis is oriented at a more acute angle with respect to the longitudinal axis of the body of the user during copulation.

SUMMARY OF THE INVENTION

The apparatus disclosed and claimed herein comprises an elongated prosthetic penis which includes an open portion for allowing direct contact between the penis and the female partner, and a base portion which provides contact with the body of the male user to support the apparatus and the pubic area and against the lower abdominal portion of the user.

Among the objects of the present invention are the following:

To provide new and useful artificial penis apparatus;

To provide new and useful elongated prosthetic penile apparatus;

To provide new and useful prosthetic penile apparatus providing an open area to allow direct contact between the user of the apparatus and his female partner;

To provide new and useful prosthetic penile apparatus including a base member connected to a tubular portion;

To provide new and useful prosthetic penile apparatus including a flange extending at an acute angle to the base, to support the apparatus against the body of the user; and To provide new and useful artificial penis apparatus including a tubular portion connected to a base member and a distal cylinder portion connected to the tubular portion by a support member.

BRIEF DESCRIPTION OF THE DRAWING

FIG. 1 is an isometric view of apparatus embodying the present invention.

FIG. 2 is a view in partial section of a portion of the apparatus of FIG. 1 taken generally along line 2—2 of FIG. 1.

FIG. 3 is an end view of the apparatus of the present invention taken generally along line 3—3 of FIG. 2.

FIG. 4 is a top view of the apparatus of the present invention.

FIG. 5 is a view in partial section taken generally along line 5—5 of FIG. 2.

FIG. 6 is a view in partial section taken generally along line 6—6 of FIG. 2.

DESCRIPTION OF THE PREFERRED EMBODIMENT

FIG. 1 is an isometric view of penile prosthetic apparatus 10 of the present invention. The apparatus includes several portions, including a belt 12, a base 20, an intermediate portion or connector 60, and an extension 70. The belt 12 is secured to the base 20 by connecting straps, including an upper connecting strap 14 and a lower connecting strap 16 which in turn are connected to the main belt loop 18. The upper and lower connecting straps 14 and 16 are shown extending from one side of the base 20 and connected to the main belt loop 18. On the opposite side of the base 20, there is another pair of connecting straps, including an upper and a lower connecting strap, which also are secured to the main belt loop 18. For convenience in using the apparatus, the main belt loop 18 may include an overlapping portion of "Velcro" material to aid in quickly and securely installing the apparatus on a person.

The base 20 is generally cylindrical in configuration with a slight inward taper towards the intermediate portion or connector 16. Extending upwardly and forwardly from the base 20 is a plate 28. The plate 28 is disposed at an angle with respect to the base and to the connector and the extension 70 so as to be disposed against the lower abdominal area of a male during use of the apparatus.

The extension 70 of the apparatus is also generally cylindrical in configuration with a closed distal end or tip 82 remote from the base. The proximate end of the extension 70, which is that end which connects with the intermediate portion or connector 60, is open. There is a slight taper from the proximate end of the extension to the closed distal end or tip 82.

The intermediate portion or connector 60 serves to connect the base 20 with the extension 70. It is gently curved between the base and the extension to provide an obtuse angle between the longitudinal axis of the base and the longitudinal axis of the extension.

FIG. 2 is a view in partial section of a portion of the apparatus of FIG. 1. The base 20, the connector 60, and the extension 70 are shown in partial section.

The base 20 is preferably made in two portions, a base or outer support portion 22 and a guide portion 32. Both portions are generally cylindrical or tubular in configuration in that they each provide an interior slightly tapered bore which receives the penis of the user. The bores are aligned with each other an are coaxial. The outer support 22 includes an outer cup 24 which curves downwardly and inwardly from an upper outer shoulder portion 23 of the base 20 adjacent the plate 28 to a lower outer shoulder portion 25 of the apparatus, which is generally in line with the connector 60. The support 22 accordingly extends more rearwardly at its upper shoulder 23 adjacent the plate 28 than at its lower shoulder 25, which may be termed the bottom of the apparatus. In use, only the upper shoulder 23 and the plate make physical contact with the lower abdominal or pubic area of the male user.

The interior bores 26 and 42 of the base support and the guide, respectively, are generally coextensive in that they present a continuous inwardly tapering bore throughout the length of the base 20.

The guide 40 includes two portions, a generally circular mouth 44, which is remote from the base support 22, and an interior or inner flange portion 46 which is adjacent and mates against the base support 22 at a circular interior shoulder 30. The base support 22 includes an outer forwardly extending flange portion 32 which is disposed over the interior or inner flange portion 46 of the guide and in turn contacts the guide at a forward shoulder 34. The shoulders 30 and 34 are both generally circular in configuration and are dimensioned so as to be substantially coextensive with the respective support and guide portions of the base 20.

A groove 48 extends about the outer periphery of the inner flange 46 of the guide 40 beneath the outer flange 32. The groove 48 receives an encircling loop of the belt 12 (see FIG. 1) which secures the belt to the base. The flange 32 includes necessary slots (not shown) through which the loops of the belt extend outwardly to join the main belt loop. The upper and lower connecting straps 14 and 16 from one side of the apparatus are illustrated in FIG. 1.

The interior bores 26 and 42 taper inwardly slightly from the cup 24 to the mouth 44. Accordingly, the diameter of the bore 42 adjacent the mouth 44 is slightly less than the diameter of the bore 26 adjacent the cup 24. Preferably, the diameter of the mouth 44 of the guide 40 is dimensioned to provide a relatively tight fit for the erected penis in order to hold the member during back and forth movements so that the apparatus 10 will move with the user. Relative motion between the user and the apparatus will accordingly not take place.

The plate 28 extends upwardly and forwardly from the upper portion of the base contact 22. The plate 28, as shown in both FIGS. 1 and 2, is a substantially flat plate, but is also flexible in order to conform to the anatomy of the user in his lower abdominal area when the apparatus is in place and in use.

The connector 60 is an intermediate portion between the base 20 and the extension 70. It includes a double concave configuration in that it curves downwardly from the base and then upwardly to the extension in a first concave configuration and then it includes a second conceve configuration longitudinally of the connector. Between the base and the extension is an elongated depression or cup 62 which extends from the bottom of the bore 42 at its lower forward part of the bore and terminates within the extension 70 at its rearward and bottom part. The cup 62 is concave to receive the underneath side or bottom of the penis. Moreover, the exterior configuration of the connector presents a curved convex outer surface 64 which is convex in two directions, matching the double concave interior. The exterior surface 64 is smooth, as are all exterior surfaces.

The longitudinal curvature of the connector 60 is designed to approximate the natural curvature of the male anatomy with which it is mated, thus lessening the artificial feeling or sensing of the apparatus 10 to both the male user and his female partner.

The extension 70 includes a converter portion 72 and a distal portion 80. The distal portion 80 is closed at the tip 82. Within the extension 70 is a tapering, smooth, cylindrical or tubular bore 74. The bore 74 tapers slightly inwardly from the entrance to the bore, which is at a converter 72 and adjacent the connector 60, to the distal portion 80 and the tip 82. The tip 82 is gently rounded, and the inside surface of the tip 82 presents a concave surface which terminates the bore 74. The entrance to the bore 74 at the converter 72 is by a gently curving opening 76 which extends upwardly and forwardly from the connector 60. The opening 76 of the converter 72 extends forwardly and upwardly to an upper termination 78. The opening 76 follows the exterior contour of the extension 70, but it extends forwardly from where the extension joins the connector 70 and upwardly in a rather uniform manner. However, at the top or upper part of the extension, the opening extends forwardly to the termination 78 with very little upward slant.

It may be seen in FIG. 2 that longitudinal axis 54 of the bores 26 and 42 of the base 20 is not coaxial with longitudinal axis 84 of the bore 74 of the extension 70. Rather, while the bores are in general alignment, longitudinally, the longitudinal axes of the respective bores intersect above the connector 60, with an obtuse angle A defined between the longitudinal axes.

For practical purposes, the tip 82 may be referred to as the forward or front portion of the apparatus, while the outer cup 24 may be referred to as the rear or back portion of the apparatus. The plate 28 extends from the upper or top portion of the apparatus, and the connector 60 is at the lower or bottom portion of the apparatus.

The base 20 is preferably relatively solid and inflexible, while the extension 70 is relatively flexible, with the distal portion 80 of the extension relatively soft, flexible, and deformable. The forward or guide portion 40 of the base is thinner with respect to the thickness of the cylindrical walls of the apparatus than at the rear or back portion of the base, and the wall thickness of the converter portion 72 of the extension is preferably thinner than the wall thickness of the guide. The wall thickness of the extension decreases from the converter 72 to the tip 82 to increase the relative deformability of the converter. The relative thickness of the intermediate or connector portion 60 is thick enough to provide substantial support and strength between the base and the extension and yet the connector is not rigid, but rather has some degree of flexibility.

FIG. 3 is a view of the apparatus of the present invention taken generally along line 3—3 of FIG. 2. It comprises an end view, looking forward, from the back or rear end of the apparatus of FIG. 2.

The upper and lower connecting straps 14 and 16 on the right side of the apparatus, looking forwardly, are shown extending outwardly from the base 20 of the apparatus 10. On the left side of the apparatus, there is a corresponding upper connecting strap 15 and a corresponding lower connecting strap 17 extending outwardly from the base and connected to the main belt loop 18 which encircles the lower torso portion of the male user of the apparatus at his upper buttocks. The upper and lower straps provide double suspension on each side of the apparatus, or a two-point suspension, extending between the main belt loop 18 of the belt 12 and the base 20 of the apparatus on each side of the apparatus, since there are two straps at the top and two at the bottom of the base 20 which securely fasten the main body encircling strap to the apparatus. A total of four suspension points are accordingly provided between the base 20 and the belt.

From the base support 22, the interior bores 26 and 42 of the base 20 extend forwardly and inwardly. At the lower front portion of the bore 42, the depression 62 extends into the bottom portion of the base and into the connector 60. The extension 70 is remote from the base 20 and, as illustrated in FIG. 3 and as disposed above, is not disposed on a coaxial alignment, but is rather disposed at an obtuse angle with respect to the axis of the bores of the base.

Extending upwardly from the top of the base 20 is the generally flat plate 28. The plate extends upwardly and forwardly at an angle which can best be seen from FIGS. 1 and 2.

FIG. 4 is a top view of the prosthetic apparatus 10. The generally inward taper of the base 20 from the outer cup 24 to the mouth 44 is clearly illustrated. Part of the inward taper of the base 20 from the cup to the mouth is shown by dotted line beneath the plate 28.

The generally rounded front tip 82 of the distal portion 80 of the extension 70 is also shown in FIG. 4. By comparing the general outline of the extension 70, particularly its distal portion 80, with that of the distal portion 80 in FIG. 4, it may be understood that the extension 70 is generally cylindrical in configuration and gently rounded at the tip 82, and is tapered inwardly towards the tip 82 from the converter 72.

The opening 76 of the extension 70 at the converter 72 extends upwardly and forwardly to the termination 78 at the top of the converter. The termination is substantially forward of the bottom portion of the opening 76 adjacent the converter 60. The upward and forward slope allows the glans of the penis to be disposed in the area of the opening 76, and partially into the bore 74 without discomfort to the user due to direct contact between the extension 70 and the glans during use of the apparatus. The relatively long open area between the mouth 44 of the base 20 and the opening 76 of the extension 70 provides for adequate direct contact between the penis of the male user and his female partner to insure direct stimulation to him. At the same time, the direct frictional contact between the female partner is increased by the length of the extension in addition to the direct contact with the user's member. However, the frictional drag to the user is minimized because of the open space between the base and the extension.

FIG. 5 is a view in partial section of the apparatus of the present invention taken generally along line 5—5 of FIG. 2. It is a view looking towards the rear or back end of the prosthetic apparatus 10 towards the base 20. The connector 60 is shown in section. The depression 62 is shown extending from within the bore 42, and at the bottom of the bore, and continuing into the connector 60. The bore 42 is shown smoothly extending and blending into the bore 26.

The plate 28 extends upwardly and forwardly at the top of the base from the top back or rear of the base. The view of FIG. 5 also illustrates the forward taper of the base 20 from the opening or cup 24 to the mouth 44, and also illustrates the relatively downward slope of the bores 26 and 42 towards the connector 60. (See also FIG 2).

The rear circular interior shoulder 30 is shown at the juncture of the forward shoulder 34 at the juncture of the guide 40 and the base support 22.

The upper connecting straps 14 and 15 and the lower connecting straps 16 and 17 are shown extending out of a plurality of slots, comprising their respective slots 50, 51, and 52, 53, of the base support 22 adjacent the forward shoulder 34. The four point suspension, two straps on the top and two straps on the bottom, of the belt is accordingly clearly illustrated in FIG. 5.

FIG. 6 is a view in partial section of the apparatus of the present invention taken generally along line 6—6 of FIG. 2. It comprises a view in partial section of the extension 70 looking forwardly toward the tip 82 of the extension 70. The bore 74 of the extension 70 is shown to be substantially cylindrical in configuration. In comparing the circular cylindrical configuration of the bore 74 in FIG. 6 with the configuration of the bore 42 at the mouth 44 of the base 20 as shown in FIG. 5, it will be seen that the cross sectional configuration of the bore 74 is substantially circular. However, referring again to FIG. 5, the cross-sectional configuration of the bore 42 at the mouth 44 is generally circular at its bottom or lower portion, but the top or upper part of the mouth appears to be flattened somewhat such that the cross-sectional configuration is not precisely circular. Rather, the radius of the mouth appears to be less at the top or upper portion from about the lateral midpoints upwardly as opposed to the relatively constant lower radius, except for the depression 62, at the mouth 44 of the guide 40. The purpose of the general flattening of the upper part of the mouth 44 of the guide 40 is to aid in guiding or directing the male member into the apparatus, and in securely holding the male member while the member is disposed within the apparatus. At the bottom of the bore 42, the purpose of the depression 62 in both the bore 42 and the connector 60 is to minimize pressure on the spongy body, or corpus spongiosum, of the penis. However, the depression 62 extends for only a short distance into the connector 70, as shown in FIGS. 2 and 4, and accordingly is not seen in FIG. 6.

While the principles of the invention have been made clear in illustrative embodiments, there will be immediately obvious to those skilled in art many modifications of structure, arrangement, proportions, the elements, materials, and components used in the practice of the invention, and otherwise, which ae particularly adapted for specific environments and operative requirements without departing from those principles. The appended claims are intended to cover and embrace any and all such modifications, within the limits only of the true spirit and scope of the invention. This specification and the appended claims have been prepared in accordance with the applicable patent laws and the rules promulgated under the authority thereof.

What is claimed is:

1. Penile prosthetic apparatus comprising, in combination:

base means, including a support portion, a plate extending upwardly and forwardly from the support portion, a first bore extending longitudinally forwardly from the support portion and terminating in a guide portion, with the diameter of the bore decreasing from the support to the guide;

extension means, including a converter portion, a second bore extending longitudinally away from the first bore and having an opening disposed toward the first bore of the base means and having a closed tip remote from the opening of the second bore; and connector means extending in a curve from the base to the extension and including a depression in the connector extending from the bore of the base means to the bore of the extension means, the curve of the connector means providing an obtuse angle between the longitudinal axis of the first bore of the base means and the longitudinal axis of the second bore of the extension means.

2. The apparatus of claim 1 in which the bore of the extension means tapers inwardly from the opening to the tip.

3. The apparatus of claim 2 in which the base means is relatively inflexible and the extension means is relatively flexible.

4. The apparatus of claim 3 in which the opening of the second bore of the extension means extends forwardly and upwardly from the connector means.

5. The apparatus of claim 4 in which the first bore of the base means includes a depression continuing the depression of the connector means.

6. The apparatus of claim 5 in which the second bore of the extension means includes a depression continuing the depression of the connector means.

7. The apparatus of claim 6 in which the base means includes belt means for securing the apparatus to a user.

* * * * *